US00PP37118P2

(12) United States Plant Patent
Rupp

(10) Patent No.: US PP37,118 P2
(45) Date of Patent: Dec. 2, 2025

(54) ***DIANTHUS* PLANT NAMED 'KLEDG27706'**

(50) Latin Name: ***Dianthus* x *allwoodii* hort.**
Varietal Denomination: KLEDG27706

(71) Applicant: KLEMM + SOHN GMBH & CO. KG, Stuttgart (DE)

(72) Inventor: Judith Rupp, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/089,983

(22) Filed: Mar. 25, 2025

(51) Int. Cl.
*A01H 5/02* (2018.01)
*A01H 6/30* (2018.01)

(52) U.S. Cl.
USPC ..... Plt./273

(58) Field of Classification Search
USPC ..... Plt./263.1, 272, 273
See application file for complete search history.

(56) References Cited

U.S. PATENT DOCUMENTS

PP24,707 P3 7/2014 Klemm et al.
PP30,672 P2 7/2019 Klemm et al.
PP35,182 P2 * 5/2023 Rupp ..... A01H 6/305 Plt./273

* cited by examiner

*Primary Examiner* — Karen M Redden
(74) *Attorney, Agent, or Firm* — Weatherly IP Solutions, LLC; James Weatherly; Karen Bechtold

(57) ABSTRACT

A new *Dianthus* plant designated 'KLEDG27706' particularly distinguished by a bi-color pattern with petals having a dark-purplish red main color and a strong reddish-purple border, and semi-double round flowers, is disclosed.

1 Drawing Sheet

Genus and species: *Dianthus* x *allwoodii* hort.
Variety denomination: 'KLEDG27706'.

BACKGROUND OF THE NEW PLANT

The present invention comprises a new and distinct variety of *Dianthus*, botanically known as *Dianthus* x *allwoodii* hort. and hereinafter referred to by the variety name 'KLEDG27706'. 'KLEDG27706' originated from a whole plant mutation of 'KLEDG12163' (U.S. Plant Pat. No. 24,707) identified in June 2020 in Stuttgart, Germany.

In June 2020, 'KLEDG27706' was first vegetatively propagated by vegetative cuttings in Stuttgart, Germany. 'KLEDG27706' was found to reproduce true to type in successive generations of asexual propagation in Stuttgart, Germany via vegetative cuttings.

SUMMARY

The following are the most outstanding and distinguishing characteristics of 'KLEDG27706' when grown under normal horticultural practices in Stuttgart, Germany.

1. Bi-color pattern with petals having a dark-purplish red main color and a strong reddish purple border; and
2. Semi-double, round flowers

DESCRIPTION OF THE PHOTOGRAPH

This new *Dianthus* plant is illustrated by the accompanying photograph of a 7-month old plant taken in May 2024 and grown in a greenhouse in Stuttgart, Germany. The colors shown are as true as can be reasonably obtained by conventional photographic procedures. The photograph is a whole plant photo of 'KLEDG27706' and shows the foliage, buds, and flowers.

DESCRIPTION

The following detailed descriptions set forth the distinctive characteristics of 'KLEDG27706'. The data which define these characteristics were collected from asexual reproductions carried out in Stuttgart, Germany. Data was collected in May 2024 from 7-month-old plants grown in a greenhouse. Color references are to The R.H.S. Colour Chart of The Royal Horticultural Society of London (R.H.S.), 5$^{th}$ edition (2007).

Classification:
*Family.*—Caryophyllaceae.
*Botanical.*—*Dianthus* x *allwoodii* hort.
*Designation.*—'KLEDG27706'.
Type.—Pot carnation.

Parentage:
*Mutation parent.*—*Dianthus* 'KLEDG12163' (U.S. Plant Pat. No. 24,707).

Plant:
*Propagation type.*—Vegetative cuttings via stem.
*Time to produce a rooted young plant.*—14 to 21 days.
*Root description.*—Fine roots, young roots are RHS 161D, mature roots are RHS 199C.
*Rooting habit shape.*—Lanceolate.
*Plant form.*—Upright.
*Plant height.*—15 cm to 17 cm.
*Plant diameter or spread.*—22 cm to 25 cm.

Lateral branches/stems:
*Shape of the branch in cross-section.*—Slightly angular.
*Hollowness of the branch.*—Absent.
*Length.*—7 cm to 10 cm.
*Diameter.*—4 cm to 7 cm.
*Internode length.*—2 cm to 3 cm.

*Internode quantity per branch.*—3 to 5.
*Number of internodes per branch/stem.*—3 to 5.
*Node length.*—0.2 cm to 0.4 cm.
*Node diameter.*—0.2 cm to 0.4 cm.
*Texture.*—Smooth.
*Color.*—RHS 146B.
*Flower clustering on the lateral branch.*—None.

Foliage:
*Arrangement.*—Opposite.
*Length.*—4 cm to 5 cm.
*Width.*—0.3 cm to 0.5 cm.
*Shape.*—Lanceolate.
*Apex.*—Acute.
*Base.*—Obtuse.
*Margin.*—Entire.
*Texture (both upper and lower surfaces).*—Smooth.
*Cross-section of the leaf.*—Moderately concave.
*Curvature of the leaf.*—Absent.
*Glaucosity of the leaf.*—Weak.
*Leaf color (both immature and mature).*—Immature: Upper surface: RHS 138A. Lower surface: RHS 137A. Mature: Upper surface: RHS 138A. Lower surface: RHS 137A.
*Venation pattern.*—Absent.

Flowers:
*Flower type and habit.*—Semi-double, round.
*Fragrance.*—Present.
*Position of the flowers compared to the foliage of the plant.*—Moderately above.
*Profile of both the upper and lower part in the lateral view.*—upper part flat convex, lower part flat.
*Diameter of the flower.*—2.0 to 2.3 cm.
*Natural flowering season.*—Spring to autumn.
*Number of flowers per spray.*—3 to 5.
*Flower longevity on the plant.*—14 to 18 days.

Buds:
*Length.*—0.5 cm to 1.5 cm.
*Diameter.*—0.3 cm to 0.4 cm.
*Shape.*—Elliptic.
*Color.*—RHS 138A.
*Extrusion of the styles at the bud stage.*—Absent.

Corolla:
*Quantity of petals and arrangement.*—7 to 13 arranged in several whorls.
*Corolla height.*—0.8 cm to 1.5 cm.
*Petal length.*—1.8 cm to 2.5 cm.
*Petal width.*—1.0 cm to 1.5 cm.
*Petal shape.*—Spoon-shaped.
*Petal apex.*—Obtuse.
*Petal base.*—Acute.
*Petal margin.*—Serrated.
*Depth of petal margin.*—Shallow.
*Petal texture (both upper and lower surfaces).*—Smooth.
*Petal color.*—Immature: Upper surface: RHS 79B main color with RHS 74A secondary color along the border of the petal. Lower surface: RHS 78C. Mature: Upper surface: RHS 59A main color with RHS 74B secondary color along the border of the petal. Lower surface: RHS 78C.
*Macule.*—Absent.

Calyx:
*Quantity of sepals and arrangement.*—Composed of 5 sepals.
*Longitudinal axis of the lobes of the calyx.*—Straight.
*Shape.*—Campanulate.
*Calyx height.*—0.8 cm to 1.5 cm.
*Calyx diameter (at the apex).*—0.4 cm to 0.6 cm.
*Sepal texture (both upper and lower surfaces).*—Smooth.
*Sepal color.*—Upper surface: RHS 137A. Lower surface: RHS 137D.
*Position of the outer lobes of the epicalyx in relation to the calyx.*—Adpressed and free.
*Apex shape of the outer lobes of the epicalyx.*—Acute.
*Tip length of the outer lobes of the epicalyx.*—0.2 cm.
*Apex shape of the inner lobes of the epicalyx.*—Short acuminate.
*Tip length of the inner lobes of the epicalyx.*—0.1 cm.

Peduncles:
*Length.*—5 cm to 8 cm.
*Diameter.*—0.2 cm.
*Strength.*—Moderate.
*Texture.*—Smooth.
*Color.*—RHS 146B.

Reproductive organs:
*Stamens.*—Quantity per flower: Moderate. Filament length: 0.5 cm to 0.8 cm. Filament color: RHS 157B. Anther length: 0.1 cm. Anther diameter: 0.05 cm. Anther color: RHS 155B. Pollen amount: None observed.
*Pistils.*—Not observed.

Seeds: None observed to May 2024.

Disease and insect resistance: No particular disease or insect resistance observed.

COMPARISON OF 'KLEDG27706' WITH PARENTAL LINE AND KNOWN VARIETY

'KLEDG27706' is distinguished from the parent as described in Table 1.

TABLE 1

Comparison with Parental Line

| Trait or characteristic | 'KLEDG27706' | 'KLEDG12163' |
|---|---|---|
| Main flower color | RHS 59A | RHS 75B |
| Secondary flower color | RHS 74B | RHS 71A |

'KLEDG27706' can be compared to the commercial *Dianthus* variety 'KLEDG18274' (U.S. Plant Pat. No. 30,672). Differences between the varieties are described in Table 2.

TABLE 2

Comparison with Similar Variety

| Trait or characteristic | 'KLEDG27706' | 'KLEDG18274' |
|---|---|---|
| Main color | RHS 59A | RHS 72C |
| Color pattern | Bi-color | Macule |

I claim:

1. A new and distinct variety of *Dianthus* plant designated 'KLEDG27706' as illustrated and described herein.

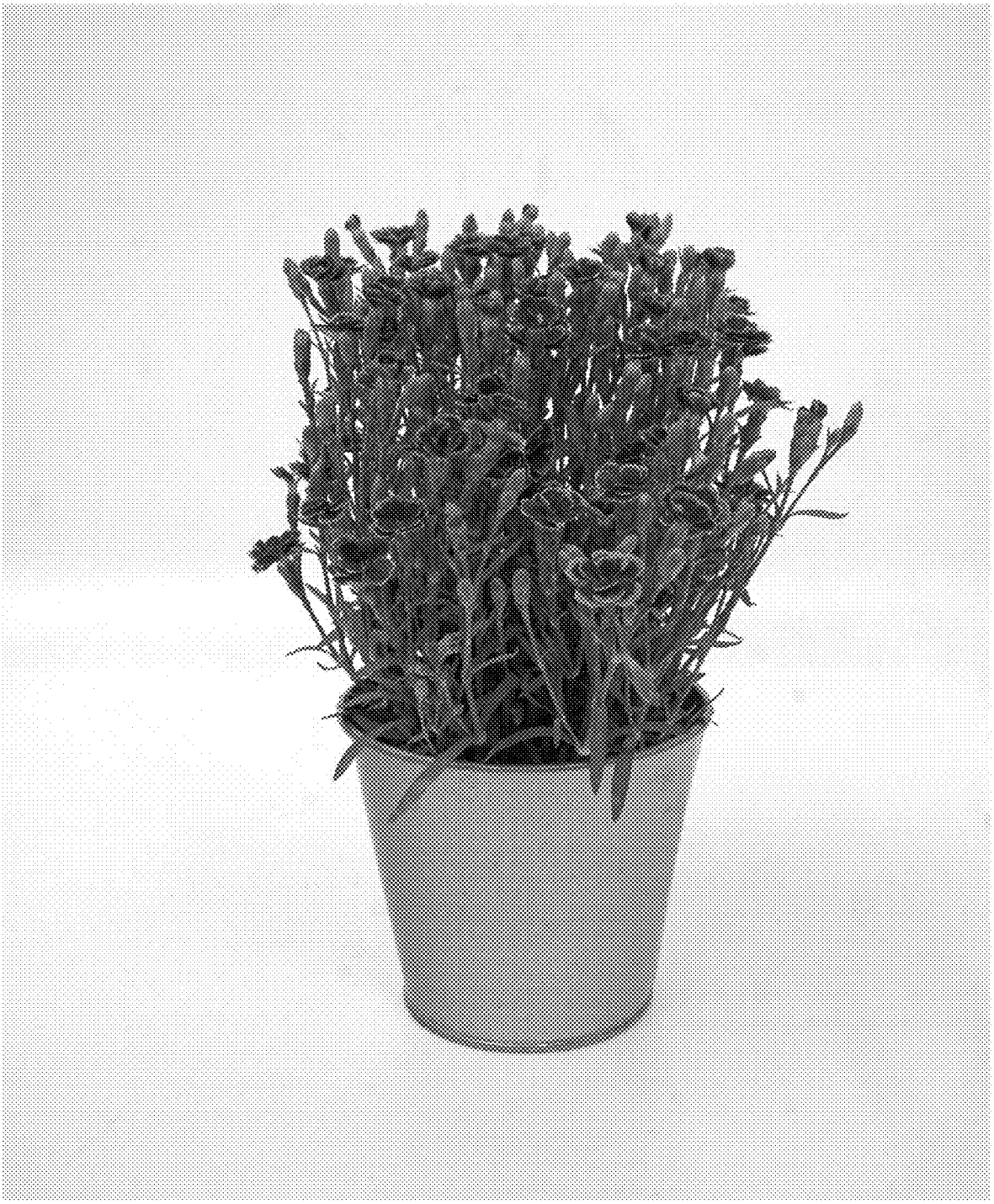

* * * * *